United States Patent
Cheung et al.

(10) Patent No.: US 7,141,709 B2
(45) Date of Patent: Nov. 28, 2006

(54) METHODS AND SYSTEMS OF PRODUCING MONOOLEFINS BY THE EXTRACTION-HYDROGENATION OF HIGHLY UNSATURATED HYDROCARBONS

(75) Inventors: Tin-Tack Peter Cheung, Kingwood, TX (US); Marvin M. Johnson, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 390 days.

(21) Appl. No.: 10/712,686

(22) Filed: Nov. 13, 2003

(65) Prior Publication Data

US 2005/0107649 A1    May 19, 2005

(51) Int. Cl.
*C07C 5/03* (2006.01)
(52) U.S. Cl. ...................................... 585/259; 585/261
(58) Field of Classification Search ................. 585/259, 585/261
See application file for complete search history.

(56) References Cited

U.S. PATENT DOCUMENTS

| | | | |
|---|---|---|---|
| 3,477,962 A | 11/1969 | Kardys | 252/412 |
| 3,651,167 A | 3/1972 | de Rosset | 260/681.5 |
| 3,666,412 A | 5/1972 | Sowards | 23/162 |
| 3,755,488 A | 8/1973 | Johnson et al. | 260/677 A |
| 3,948,808 A | 4/1976 | Box, Jr. et al. | 252/462 |
| 3,957,688 A | 5/1976 | Farha, Jr. et al. | 252/455 R |
| 4,128,595 A | 12/1978 | Montgomery | 260/677 H |
| 4,191,846 A | 3/1980 | Farha, Jr. et al. | 585/440 |
| 4,227,025 A | 10/1980 | Montgomery | 585/259 |
| 4,484,015 A | 11/1984 | Johnson et al. | 585/262 |
| 4,571,442 A * | 2/1986 | Cosyns et al. | 585/261 |
| 4,906,800 A | 3/1990 | Henry et al. | 585/260 |
| 5,413,984 A | 5/1995 | Marecot et al. | 502/333 |
| 5,475,173 A | 12/1995 | Cheung et al. | 585/259 |
| 5,489,565 A | 2/1996 | Cheung et al. | 502/325 |
| 6,040,489 A | 3/2000 | Imai | |
| 6,127,588 A | 10/2000 | Kimble et al. | 585/260 |
| 6,130,260 A | 10/2000 | Hall et al. | |
| 6,323,247 B1 | 11/2001 | Hall et al. | |
| 6,433,235 B1 | 8/2002 | Cantrell | |
| 6,602,920 B1 | 8/2003 | Hall et al. | |
| 6,635,600 B1 | 10/2003 | Kimble et al. | 502/330 |
| 2004/0002553 A1 | 1/2004 | Hall et al. | |
| 2005/0048658 A1 | 3/2005 | Johnson et al. | |

(Continued)

FOREIGN PATENT DOCUMENTS

EP    0722776    7/1996

(Continued)

OTHER PUBLICATIONS

PCT International Search Report, PCT/US2004/038132, Mar. 23, 2005.

*Primary Examiner*—Thuan Ding Dang
(74) *Attorney, Agent, or Firm*—Rodney B. Carroll; K. KaRan Reed; David W. Dockter (57) ABSTRACT

In some embodiments, methods of producing monoolefins include contacting an olefin stream with a polar solvent to extract a highly unsaturated hydrocarbon from the olefin stream, followed by contacting the polar solvent with a hydrogenation catalyst in the presence of hydrogen at conditions effective to hydrogenate the highly unsaturated hydrocarbon to a monoolefin. The monoolefin then desorbs from the polar solvent and enters the purified olefin stream, allowing the polar solvent to be recycled. In other embodiments, monoolefin production systems include an extraction-hydrogenation zone for performing the extraction and hydrogenating steps in situ. In alternative embodiments, the hydrogenation zone is disposed downstream from the extraction zone.

49 Claims, 4 Drawing Sheets

U.S. PATENT DOCUMENTS

| | | |
|---|---|---|
| 2005/0049445 A1 | 3/2005 | Johnson et al. |
| 2005/0065391 A1 | 3/2005 | Gattis et al. |
| 2005/0065392 A1 | 3/2005 | Peterson et al. |

FOREIGN PATENT DOCUMENTS

| | | |
|---|---|---|
| GB | 832639 | 4/1960 |
| GB | 1403556 | 8/1975 |
| WO | WO0064846 | 2/2000 |
| WO | WO2005/025746 | 3/2005 |
| WO | WO2005/026086 | 3/2005 |
| WO | WO2005/035689 | 4/2005 |
| WO | WO2005/035690 | 4/2005 |

* cited by examiner

METHODS AND SYSTEMS OF PRODUCING MONOOLEFINS BY THE EXTRACTION-HYDROGENATION OF HIGHLY UNSATURATED HYDROCARBONS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present invention relates to the production of monoolefins, and more particularly to methods and systems of producing monoolefins by extracting highly unsaturated hydrocarbons from an olefin stream and hydrogenating them to monoolefins.

BACKGROUND OF THE INVENTION

Monoolefins such as ethylene and propylene are often employed as monomers in preparing various polymers. Monoolefins may be produced by the thermal or catalytic cracking of refinery gas, ethane, propane, butane, and the like. Monoolefins produced in this manner usually contain acetylenes and diolefins that adversely affect polymer production. Thus, to form a polymer grade monoolefin, the amount of acetylenes and diolefins in a monoolefin stream recovered is typically reduced to form a polymer grade monoolefin.

One technique that has been used to reduce the amount of acetylenes and diolefins in a monoolefin stream involves hydrogenating the acetylenes and diolefins in the gas phase to monoolefins using catalysts comprising palladium and an inorganic support. Unfortunately, this total gas phase hydrogenation process does not entirely eliminate the acetylenes and the diolefins from the monoolefin stream. Further, in some applications total gas phase hydrogenation units produce green oil as a side-product by oligomerizing the acetylenes and diolefins. As used herein, green oil refers to molecules having 6 or more carbon atoms per molecule that undesirably foul the hydrogenation catalyst, causing the catalyst to deactivate. The deactivation of the hydrogenation catalyst results in the catalyst having a lower activity and selectivity to monoolefins. Consequently, the cycle time of total gas phase hydrogenation units are shortened by the presence of such green oil. Thus, the hydrogenation catalyst frequently requires regeneration, causing the operation costs of the hydrogenation process to be very high. Another technique that has been employed to reduce the acetylene content in a monoolefin stream has been the extractive distillation of the acetylenes. The extracted acetylenes have less commercial value than ethylene.

Therefore, a need exists for a less expensive process that improves removal of acetylenes and diolefins from a monoolefin stream without experiencing much fouling and that results in conversion of the acetylene to higher value chemicals. That is, it is desirable to extend the catalyst life and increase the selectivity of the hydrogenation catalyst to monoolefins such as ethylene.

SUMMARY OF THE INVENTION

In an embodiment, methods of producing monoolefins include contacting an olefin stream with a polar solvent such that a highly unsaturated hydrocarbon in the olefin stream becomes dissolved in the polar solvent. The methods further include contacting the polar solvent with a hydrogenation catalyst in the presence of hydrogen at conditions effective to hydrogenate the highly unsaturated hydrocarbon to a monoolefin such as ethylene. The monoolefin then desorbs from the polar solvent and enters the olefin stream, allowing the polar solvent to be recycled. The olefin stream may comprise, for example, cracked gas recovered from an ethylene cracker, ethylene separated from cracked gas, propylene separated from cracked gas, or combinations thereof. The highly unsaturated hydrocarbon may comprise, for example, an acetylene, a diolefin, or combinations thereof. In another embodiment, monoolefin products are made by the method described above.

In an alternative embodiment, monoolefin production systems include an extraction-hydrogenation zone for extracting a highly unsaturated hydrocarbon from an olefin stream into a polar solvent and, in situ, hydrogenating the highly unsaturated hydrocarbon to a monoolefin. A liquid-gas separation zone for separating the monoolefin from the polar solvent by desorption of the monoolefin may be disposed downstream from the extraction-hydrogenation zone.

In yet another embodiment, monoolefin production systems include an extraction zone for extracting a highly unsaturated hydrocarbon from an olefin stream into a polar solvent and a hydrogenation zone for hydrogenating the highly unsaturated hydrocarbon in the polar solvent to a monoolefin. The hydrogenation zone is disposed downstream from the extraction zone. In addition, a liquid-gas separation zone for separating the monoolefin from the polar solvent by desorption of the monoolefin may be disposed downstream from the hydrogenation zone.

DESCRIPTION OF THE DRAWINGS

The invention, together with further advantages thereof, may best be understood by reference to the following description taken in conjunction with the accompanying drawings in which.

DETAILED DESCRIPTION OF THE INVENTION

Figure 1:
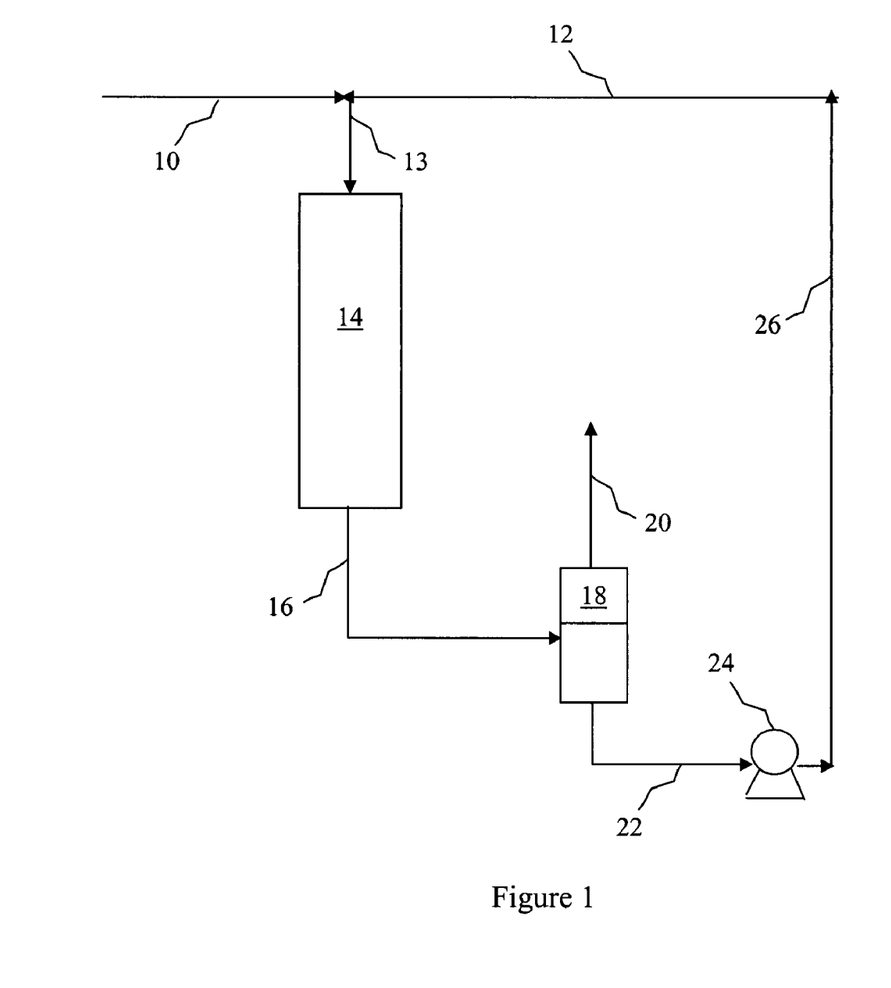
FIG. 1 depicts a process flow diagram of an embodiment in which an olefin stream is fed to an extraction-hydrogenation reactor for in situ extraction of a highly unsaturated hydrocarbon from the olefin stream and hydrogenation of the highly unsaturated hydrocarbon to a monoolefin.

FIG. 1 illustrates embodiments of an extraction-hydrogenation process and system for producing monoolefins. In the extraction-hydrogenation process, an olefin stream is contacted with a polar solvent such that a highly unsaturated hydrocarbon in the olefin stream becomes dissolved in the polar solvent. The polar solvent containing the highly unsaturated hydrocarbon is then contacted with a hydrogenation catalyst in the presence of hydrogen at conditions effective to hydrogenate the highly unsaturated hydrocarbon to a monoolefin. The extraction-hydrogenation system includes an extraction-hydrogenation zone for extracting a highly unsaturated hydrocarbon from an olefin stream into a polar solvent and, in situ, hydrogenating the highly unsaturated hydrocarbon to a monoolefin. A liquid-gas separation zone for separating the monoolefin from the polar solvent by desorption of the monoolefin may be disposed downstream from the extraction-hydrogenation zone.

As shown in FIG. 1, the extraction-hydrogenation process includes combining a first feed stream 10 comprising an olefin stream and hydrogen ($H_2$) with a second feed stream 12 comprising a polar solvent, thereby forming a stream 13 that is fed to an extraction-hydrogenation reactor 14. In this manner, the olefin stream is contacted with the polar solvent before being fed to reactor 14. Alternatively, the two feed streams 10 and 12 could be separately fed to reactor 14.

In one embodiment, the olefin stream may be recovered from an olefin production unit such as a thermal or catalytic hydrocracker, e.g., an ethylene cracker, and thus may comprise any of the product streams from the olefin production unit. For example, the olefin stream may comprise all of the cracked gas recovered from an ethylene cracker, including olefins (i.e., hydrocarbons whose molecules contain a pair of carbon atoms linked together by a double bond) such as ethylene and propylene. In addition to olefins, the olefin stream may contain $H_2$ and highly unsaturated hydrocarbons such as acetylenes and diolefins. As used herein, "highly unsaturated hydrocarbons" refers to hydrocarbons whose molecules contain a triple bond or two or more double bonds in a molecule. Examples of such highly unsaturated hydrocarbons include, but are not limited to, acetylene, methylacetylene, vinylacetylene, ethylacetylene, 2-butyne, propadiene, butadiene, isoprene, 1,3-pentadienes, cyclopentadiene, and combinations thereof. In other embodiments, the olefin stream may comprise ethylene separated from cracked gas, propylene separated from cracked gas, or combinations thereof.

As mentioned above, if the olefin stream is recovered from an olefin production unit, it may already contain $H_2$. However, if the olefin stream does not contain $H_2$ or it contains an insufficient amount of $H_2$, the $H_2$ can be separately added to the olefin stream to form first feed stream 10. The amount of $H_2$ combined with the olefin stream may be selected such that a molar ratio of the $H_2$ to the highly unsaturated hydrocarbons in the olefin stream is in the range of from about 0.5 to about 20, alternatively from about 1 to about 10, or from about 2 to about 5.

The amount of polar solvent in feed stream 12 may be pre-selected to dissolve the maximum allowable amount of highly unsaturated hydrocarbon while minimizing capital cost. For example, the weight ratio of the polar solvent to the highly unsaturated hydrocarbon in the stream 13 may be in the range of from about 0.00006 to about 0.15, alternatively from about 0.0003 to about 0.03, or from about 0.0006 to about 0.015. Examples of suitable polar solvents include, but are not limited to, N-methylpyrrolidone (NMP), formamide, N-methylformamide, N-ethylformamide, N-phenylformamide, N,N-dimethylformamide (DMF), N,N-diethylformamide, N,N-diphenylformamide, N-methylpyrrolidone, sulfolane, n-formyl morpholine, glycerol, triethylene glycerol, tetraethylene glycerol, or combinations thereof.

In some embodiments, stream 12 also contains a high boiling additive that is combined with the polar solvent before feeding it to reactor 14. As used herein, "high boiling additive" refers to a chemical that when added to the polar solvent exhibits very low vapor pressure, allowing the additive to remain with the polar solvent during the hydrogenation process described below. Examples of suitable high boiling additives include, but are not limited to, triphenylphosphine, diphenylphosphine, benzothiophene, dibenzothiophene, substituted dibenzothiophenes, pyridine, substituted pyridines, aniline, substituted anilines, alkali metal fluorides, or combinations thereof. The amount of high boiling additive in stream 12 may range from about 0.0001 to about 10 weight percent (wt. %), alternatively from about 0.001 to about 1 wt. %, or from about 0.01 to about 0.1 wt. %, all weight percentages being based on the total weight of the mixture.

An extraction-hydrogenation zone is located within reactor 14. Thus, reactor 14 is operated at conditions effective for in situ extraction and hydrogenation of highly unsaturated hydrocarbons to form monoolefins. In particular, the conditions within reactor 14 are effective for the polar solvent to extract the highly unsaturated hydrocarbons, e.g., acetylenes and diolefins, from the olefin stream. As such, the highly unsaturated hydrocarbons dissolve in the polar solvent and thus become part of the liquid phase. In the case where the olefin stream comprises all of the cracked gas recovered from an ethylene cracker (i.e., raw cracked gas), removing the highly unsaturated hydrocarbons in a single extraction step makes the subsequent separation of the olefin products more efficient. That is, no separate purification steps such as distillations are required to remove the highly unsaturated hydrocarbons from the olefin products. When the olefin stream comprises ethylene separated from cracked gas, the polar solvent may extract acetylene from the ethylene. When the olefin stream comprises propylene separated from cracked gas, the polar solvent may extract methylacetylene and propadiene from the propylene.

The conditions within reactor 14 are also effective to selectively hydrogenate highly unsaturated hydrocarbons in the liquid phase to monoolefins upon contacting a hydrogenation catalyst in the presence of the $H_2$. The conditions are desirably effective to maximize hydrogenation of the highly unsaturated hydrocarbons to monoolefins and to minimize hydrogenation of the highly unsaturated hydrocarbons to alkanes. As used herein, "monoolefins" refer to hydrocarbons whose molecules contain one pair of carbon atoms linked together by a double bond, and "alkanes" refers to hydrocarbons whose molecules contain pairs of carbon atoms linked together only by single bonds. For example, acetylene may be hydrogenated to ethylene. The temperature within the extraction-hydrogenation zone may be, for example, in the range of from about 10° C. to about 300° C., alternatively from about 20° C. to about 250° C., or from about 30° C. to about 200° C. Further, the pressure within the extraction-hydrogenation zone may be, for example, in the range of from about 15 to about 2,000 pounds per square inch gauge (psig), alternatively from about 50 to about 1,500 psig, or from about 100 to about 1,000 psig.

The hydrogenation catalyst contained in reactor 14 may be arranged in any suitable configuration such as a fixed bed.

The hydrogenation catalyst may comprise palladium (Pd) supported by an inorganic material known as a support. Examples of a suitable inorganic support include, but are not limited to, alumina, silica, titania, zirconia, aluminosilicates (clays and/or zeolites), a spinel such as zinc aluminate, zinc titanate, and magnesium aluminate, or combinations thereof. The palladium may be, for example, in the form of palladium metal or palladium oxide that is disposed near the surface of the inorganic support. The hydrogenation catalyst may also include a selectivity enhancer such as silver, silver compounds, phosphorus, sulfur, phosphorus compounds, sulfur compounds, potassium, potassium compounds, or combinations thereof. Examples of suitable selectivity enhancer compounds include, but are not limited to, silver, silver nitrate, silver chloride, potassium phosphate, sodium phosphate, ammonium phosphate, sodium sulfate, potassium sulfate, ammonium sulfate, or combinations thereof. The selectivity enhancer may be distributed throughout the support. Further, the hydrogenation catalyst may optionally include fluorine or a fluoride compound such as non-alkali metal fluorides, e.g., ammonium fluoride, hydrogen fluoride, and ammonium hydrogen fluoride; alkali metal fluorides, e.g., potassium fluoride, sodium fluoride, rubidium fluoride, and cesium fluoride; or combinations thereof. In some embodiments, the hydrogenation catalyst is $Pd/Ag/Al_2O_3$ or $Pd/Ag/KF/Al_2O_3$. Additional disclosure related to hydrogenation catalysts for selectively hydrogenating highly unsaturated hydrocarbons to monoolefins can be found in U.S. Pat. No. 6,127,588, which is incorporated by reference herein in its entirety.

During the hydrogenation of the highly unsaturated hydrocarbons within reactor 14, the polar solvent continuously removes all or a portion of any oligomers, i.e., green oil, that forms on the hydrogenation catalyst. As such, the polar solvent serves to reduce the amount of fouling of the hydrogenation catalyst by green oil, thus extending the life of the catalyst. Consequently, the catalyst requires regeneration less often, resulting in lower operating costs of the hydrogenation process. Extraction using the polar solvent may be particularly useful in olefin production plants that produce heavier olefins and in olefin production plants that tend to crack heavier feeds and produce heavier highly unsaturated hydrocarbons. Such heavier olefins and heavier highly unsaturated hydrocarbons are more likely to form oligomers on the hydrogenation catalyst.

In embodiments in which the polar solvent contains a high boiling additive, the additive remains in the polar solvent during and after the hydrogenation process due to its high boiling nature. Without intending to be limited by theory, it is believed that the high boiling additive modifies the catalyst in such a way as to greatly increase the selectivity to monoolefins during the hydrogenation. It is believed that the selectivity to monoolefins is also increased by the extraction of the highly unsaturated hydrocarbons into the polar solvent such that the polar solvent is enriched with the highly unsaturated hydrocarbons. The selectivity to monoolefins may be greater than about 30%, alternatively greater than about 50%, or greater than about 80%.

The monoolefins produced in the extraction/hydrogenation zone, the polar solvent, the olefin stream, and any unconverted reactants (i.e., $H_2$ and highly unsaturated hydrocarbons) exit reactor 14 via effluent stream 16 and are passed to a liquid-gas separator 18. Since the monoolefins have lower solubilities in the polar solvent than the highly unsaturated hydrocarbons, the monoolefins desorb from the liquid polar solvent and enter the gaseous phase in situ within reactor 14 and/or separator 18. The gases contained in liquid-gas separator 18 e.g., the purified olefin stream which is substantially absent of highly unsaturated hydrocarbons, rise to the top of separator 18, where they exit the separator via gas stream 20. The polar solvent is drawn off the bottom of liquid-gas separator 18 via liquid stream 22 and is passed to a recycle pump 24. The recycle pump 24 then pumps the polar solvent in a recycle stream 26 back to stream 12 for recycling to reactor 14. In the case where a high boiling additive is present in the polar solvent, the high boiling additive is also recycled back to reactor 14. The removal of green oil from the polar solvent recirculation defined by liquid streams 22, 26 and 12 is known to those skilled in the art. For example, the skilled artisan would understand that the green oil could be removed from the polar solvent via liquid-liquid extraction.

Figure 2:
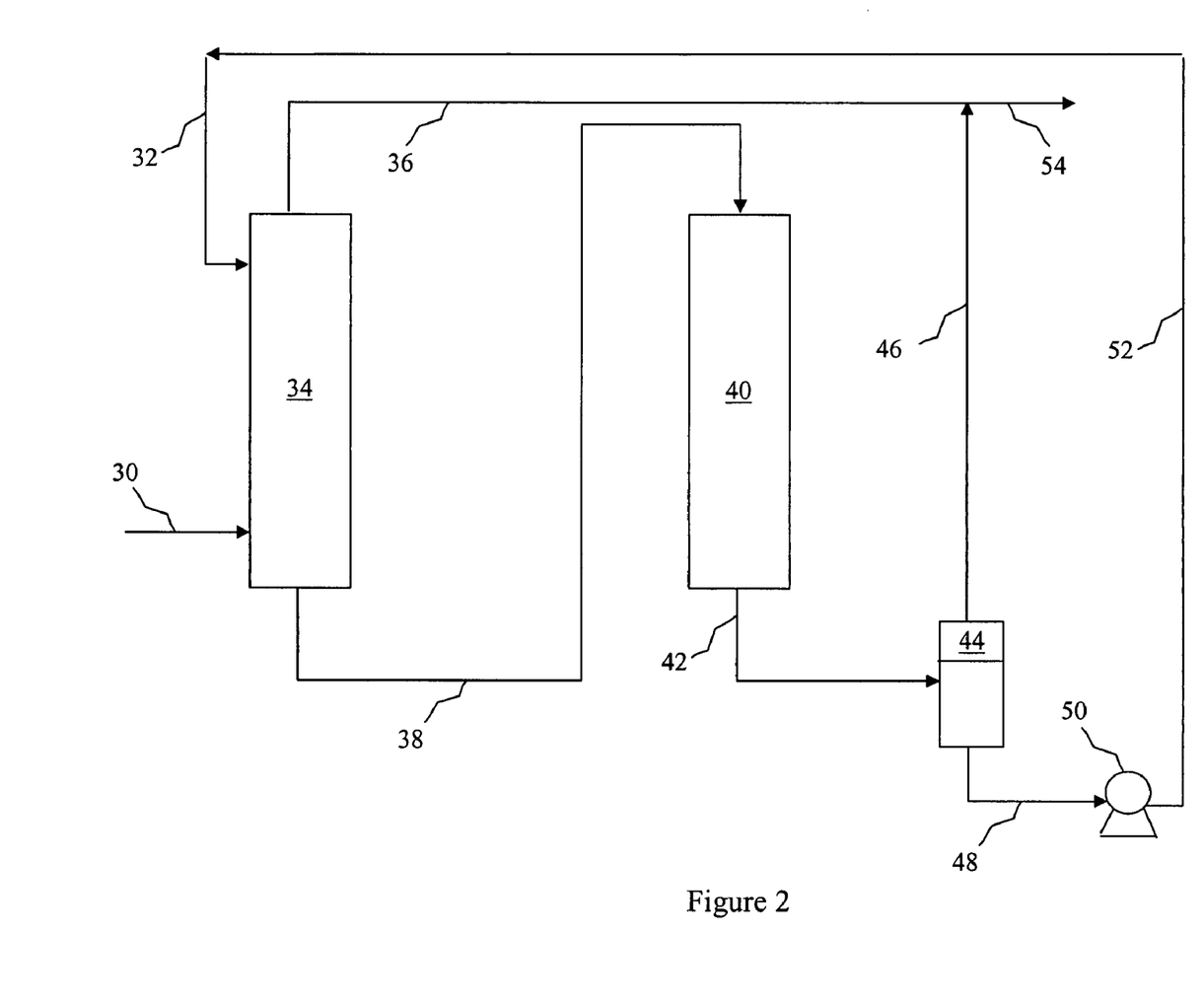
FIG. 2 depicts a process flow diagram of an alternative embodiment in which the hydrogenation reactor is downstream from the extraction unit.

FIG. 2 illustrates embodiments of an extraction-hydrogenation process and a system for producing monoolefins that are similar to the embodiments shown in FIG. 1. However, the process and system shown in FIG. 2 employ two separate zones for the extraction of the highly unsaturated hydrocarbons from an olefin stream and the hydrogenation of the highly unsaturated hydrocarbons to monoolefins. In these embodiments, the hydrogenation zone is disposed downstream from the extraction zone.

In particular, the extraction-hydrogenation process shown in FIG. 2 includes feeding an olefin stream 30 and a polar solvent stream 32 to an extraction unit 34. These two streams 30 and 32 may be fed separately to extraction unit 34, as shown, or they may be combined and fed together in a single stream to extraction unit 34. The olefin stream 30 and the polar solvent stream 32 may include the same materials in the same amounts as the olefin stream 10 and the polar solvent stream 12 described above in reference to FIG. 1. The polar solvent may also contain a high boiling additive like that described in reference to FIG. 1.

Within extraction unit 34, the olefin stream and the polar solvent are contacted in an extraction zone operated at conditions effective to extract the highly unsaturated hydrocarbons from the olefin stream into the polar solvent. In an embodiment, the extraction zone is a gas-liquid extraction column. The internal design of the gas-liquid extraction column is known to those skilled in the art. The extraction zone thus may be operated under conditions optimized for a gas-liquid extraction, and this optimization is known to those skilled in the art. For example, the skilled artisan would understand that operation at elevated pressures and lower temperatures benefits the extraction efficiency. The purified olefin stream, which is substantially absent of the highly unsaturated hydrocarbons, is then separated from the polar solvent in which the highly unsaturated hydrocarbons are dissolved. That is, the gaseous olefin stream is allowed to exit the extraction unit 34 via an overhead stream 36 while the liquid polar solvent is drawn off the bottom of extraction unit 34 via stream 38. The polar solvent stream 38 is then fed to a hydrogenation reactor 40 containing a hydrogenation catalyst like that described above in reference to FIG. 1. If contained in stream 32, the high boiling additive would remain present in polar solvent stream 38. In addition, $H_2$ may be combined with polar solvent stream 38 before that stream is fed to hydrogenation reactor 40.

A hydrogenation zone disposed in hydrogenation reactor 40 is operated at conditions effective to selectively hydrogenate the highly unsaturated hydrocarbons in the liquid phase to monoolefins as they contact the hydrogenation catalyst in the presence of the $H_2$. These operating conditions may be the same as those of the extraction-hydrogenation zone described above in reference to FIG. 1. As described previously, the polar solvent washes green oil from the hydrogenation catalyst such that the catalyst no longer needs to be frequently regenerated. Also, if present, the high boiling additive in the polar solvent increases the selectivity to monoolefins.

The monoolefins produced in the hydrogenation zone, the polar solvent, and any unconverted reactants (i.e., $H_2$ and highly unsaturated hydrocarbons) exit hydrogenation reactor 40 via effluent stream 42 and are passed to a liquid-gas separator 44. A gas stream 46 comprising any remaining $H_2$ and monoolefins that desorb from the liquid phase and enter the gas phase exits liquid-gas separator 44. The desorption of the monoolefins may be caused by lowering the pressure in separator 44 to, for example, 50 psig. The gas stream 46 is then combined with olefin stream 36 from which the highly unsaturated hydrocarbons have been removed, thereby increasing the amount of monoolefins recovered in a product stream 54. The polar solvent is drawn off the bottom of liquid-gas separator 44 via liquid stream 48 and is passed to a recycle pump 50. The recycle pump 24 then pumps the polar solvent in a recycle stream 52 back to feed stream 32 for recycling to extraction unit 34. In the case where a high boiling additive is present in the polar solvent, the high boiling additive is also recycled back to extraction unit 34. The removal of green oil from the polar solvent recirculation defined by liquid streams 48, 52 and 32 is known to those skilled in the art. For example, the skilled artisan would understand that the green oil could be removed from the polar solvent via liquid-liquid extraction.

EXAMPLES

The invention having been generally described, the following examples are given as particular embodiments of the invention and to demonstrate the practice and advantages thereof. It is understood that the examples are given by way of illustration and are not intended to limit the specification or the claims to follow in any manner.

Example 1

This example illustrates performing an extraction-hydrogenation process in which two different solvents are used to extract acetylene from an ethylene stream and the acetylene is converted to ethylene, wherein one solvent is a polar solvent, i.e., DMF/KF, and the other solvent is a nonpolar solvent, i.e., n-propylbenzene. The first run was performed in accordance with the following procedure. Ten milliliters (mL) of a Pd/Ag catalyst containing 0.3 wt % Pd and 1.6 wt % Ag on an alumina support was placed in a ½ inch ID Stainless Steel reactor, all weight percentages being based on the weight of the total catalyst. The catalyst was washed twice with 200 mL of fresh DMF. Then 200 mL of a polar solvent containing 346 ppm of KF in DMF was added to the product separator of the reactor. The catalyst was then reduced overnight under a 100 cc/min flow of hydrogen at 100 psig. The polar solvent was subsequently circulated through the reactor at a flow rate of 2.1 cc/min. A feed gas containing about 1.3 mole % acetylene and 43 mole % ethylene, based on the moles of the total feed, was passed into the reactor at a flow rate of 430 cc/min. Also, a stream of hydrogen was passed into the reactor at a flow rate of 12 cc/min, and the reactor was operated at a pressure of 200 psig. The DMF/KF solvent extracted acetylene from the feed gas such that the acetylene became dissolved in the liquid phase. As the acetylene in the DMF/KF solvent contacted the catalyst, it was hydrogenated to ethylene, which desorbed from the liquid phase into the gas phase. The same procedure was followed for the second run except that n-propylbenzene was employed as the solvent to serve as a control.

Figure 3:
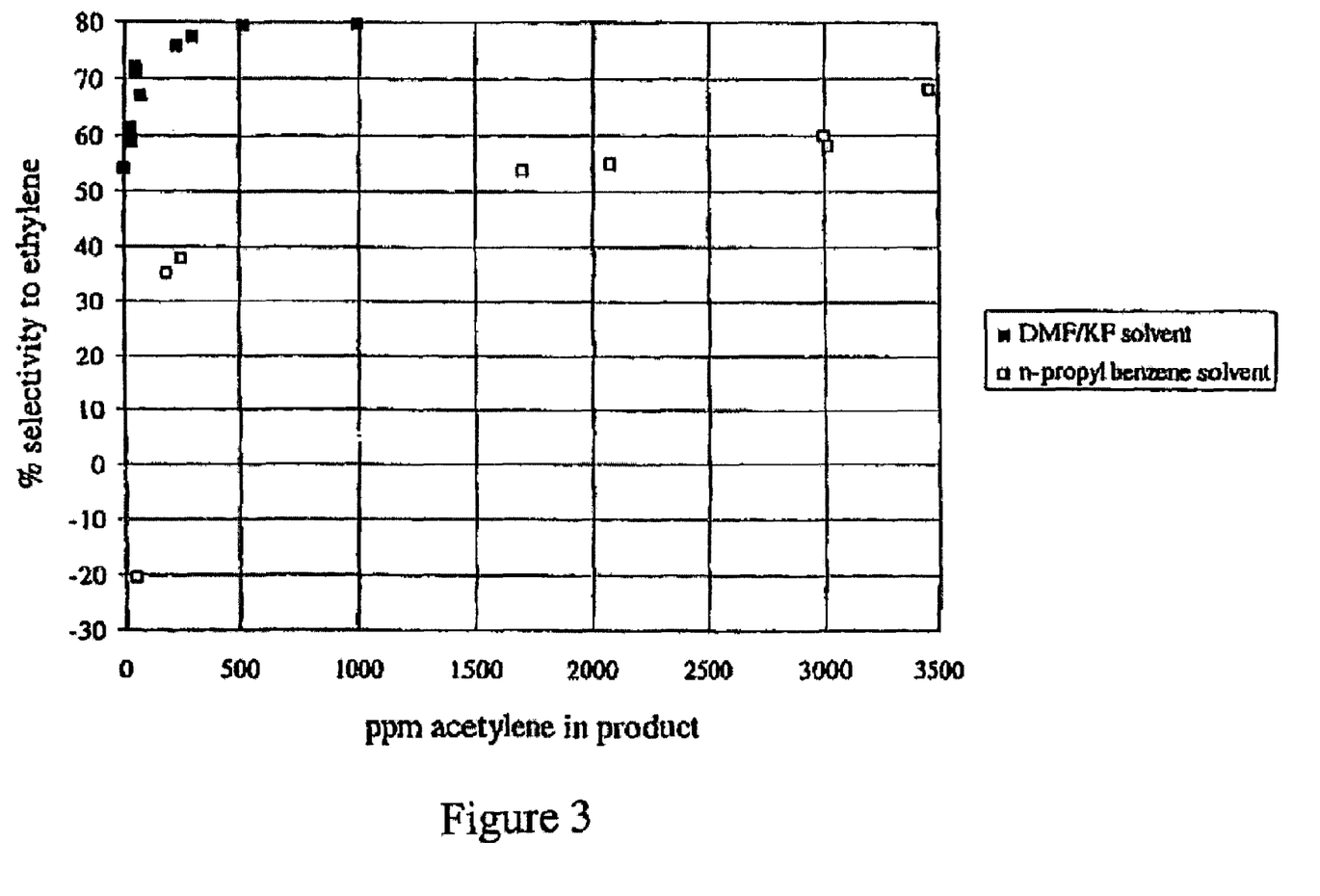
FIG. 3 depicts a plot of the % selectivity to ethylene as a function of the amount of acetylene in the product of an extraction-hydrogenation process.

FIG. 3 depicts a plot of the % selectivity to ethylene as a function of the amount of acetylene in the product for both of the runs described above. The results shown in FIG. 3 demonstrate that the selective hydrogenation of acetylene to extinction is attainable in the presence of a highly polar solvent. FIG. 3 also illustrates that as the % conversion of acetylene achieved by the catalyst increases, the selectivity decreases. Moreover, FIG. 3 shows that a polar extraction solvent such as DMF results in a higher selectivity than a non-polar extraction solvent such as n-propylbenzene.

Example 2

In this example, an extraction-hydrogenation process was performed in which a polar solvent (i.e., DMF) containing a high boiling point additive (i.e., triphenylphosphine) was used to remove acetylene from a hydrocarbon stream, and then the acetylene was converted to ethylene. For comparison, an extraction-hydrogenation process in which the polar solvent did not contain the high boiling point additive was also performed. The following procedure was followed in runs 1–3. About 10 mL of a catalyst containing 0.5 wt. % Pd, 2.55 wt. % Ag, 1.4 wt. % K as KF (all weight percentages being by weight of the total catalyst), and a zinc aluminate support was placed in a 0.5 inch ID Stainless Steel reactor. The catalyst was reduced by heating it at 200° F. over a period of about 48 hours and then at 300° F. for an additional 3 hours in the presence of $H_2$. The reactor was then cooled, followed by injecting 102 grams of DMF in the product separator. The mixture in the product separator was circulated through the reactor at a flow rate of 1.1 ml/min in run 1, 1.5 mL/min in run 2, and 2.0 ml/min in run 3. A feed gas containing about 1.8 mole % acetylene and about 45 mole % ethylene, based on the moles of the total feed, was passed into the reactor at 400 mL/min and 200 psig. Also, a stream of hydrogen was passed into the reactor at a flow rate of 12 cc/min. Additional components contained in the feed gas are shown in Table 1 below. The DMF extracted acetylene from the feed gas such that the acetylene was dissolved in the DMF in the liquid phase. As the acetylene in the DMF contacted the catalyst, it was hydrogenated to ethylene, which desorbed from the liquid phase. The reaction pressure was 200 psig. Additional details regarding runs 1–3 are provided in Table 1 below.

The same procedure was followed for runs 4–5 except that 0.0101 gram of triphenylphosphine dissolved in 1 gram of DMF was injected into the product separator, which still contained the DMF from run 1–3. The flow rate of the solvent was set at 1.7 mL/min for run 4 and 1.55 mL/min for run 5. For runs 6–8, about 1 gram of the DMF remaining in the product separator after runs 4–5 was removed and mixed with 0.0160 gram of triphenylphosphine. The resulting mixture was injected into the product separator and circulated through the reactor at a flow rate of 1.9 mL/min for run 6, 1.7 mL/min for run 7, and 1.6 mL/min for run 8. The same procedure as that used in runs 1–3 was also followed for runs 9–10 except that 0.0250 gram of triphenylphosphine was added to 1.45 gram of DMF before injecting the resulting mixture into the product separator. The solvent flow rate was set at 1.9 mL/min for run 9 and 2.0 mL/min for run 10. Additional details regarding runs 4–10 can be seen in Table 1 below.

TABLE 1

|  | Feed Stream | Run #1 Effluent Stream | Run #2 Effluent Stream | Run #3 Effluent Stream | Run #4 Effluent Stream | Run #5 Effluent Stream | Run #6 Effluent Stream | Run #7 Effluent Stream | Run #8 Effluent Stream | Run #9 Effluent Stream | Run #10 Effluent Stream |
|---|---|---|---|---|---|---|---|---|---|---|---|
| Temperature, °F. |  | 253 | 252 | 253 | 251 | 253 | 251 | 253 | 255 | 254 | 254 |
| C6+, mole % | 0.000 | 0.005 | 0.009 | 0.011 | 0.013 | 0.013 | 0.013 | 0.015 | 0.016 | 0.066 | 0.062 |
| Methane, mole % | 53.453 | 53.342 | 53.288 | 53.242 | 53.426 | 53.311 | 53.480 | 53.337 | 53.124 | 53.295 | 53.247 |
| Ethane + Ethylene, mole % | 44.735 | 46.590 | 46.631 | 46.673 | 46.498 | 46.610 | 46.445 | 46.577 | 46.785 | 46.566 | 46.618 |
| Acetylene, mole % | 1.812 | 0.004 | 0.003 | 0.007 | 0.004 | 0.004 | 0.005 | 0.005 | 0.006 | 0.006 | 0.006 |
| Butane, mole % | 0.000 | 0.000 | 0.000 | 0.000 | 0.000 | 0.000 | 0.000 | 0.000 | 0.000 | 0.000 | 0.000 |
| 1-butene, mole % | 0.000 | 0.038 | 0.044 | 0.043 | 0.036 | 0.038 | 0.034 | 0.043 | 0.046 | 0.039 | 0.040 |
| Trans-2-butene, mole % | 0.000 | 0.018 | 0.019 | 0.022 | 0.019 | 0.019 | 0.016 | 0.020 | 0.020 | 0.019 | 0.018 |
| Cis-2-butene, mole % | 0.000 | 0.007 | 0.009 | 0.009 | 0.008 | 0.009 | 0.007 | 0.008 | 0.009 | 0.009 | 0.009 |
| Ethylene/Ethane molar ratio | 1376.733 | 67.187 | 71.709 | 72.997 | 88.697 | 92.689 | 100.693 | 114.755 | 111.926 | 111.357 | 114.399 |
| DMF recycle rate, cc/min. |  | 1.100 | 1.500 | 2.000 | 1.700 | 1.550 | 1.900 | 1.700 | 1.600 | 1.900 | 2.000 |
| Triphenylphosphine, g/100 g DMF |  | 0 | 0 | 0 | 0.01 | 0.01 | 0.026 | 0.026 | 0.026 | 0.051 | 0.051 |
| % Selectivity to ethylene |  | 57.04 | 58.38 | 58.66 | 66.15 | 66.98 | 70.21 | 71.67 | 70.55 | 71.43 | 72.01 |
| % Acetylene conversion |  | 99.78 | 99.83 | 99.61 | 99.78 | 99.78 | 99.72 | 99.72 | 99.67 | 99.67 | 99.67 |

Figure 4:
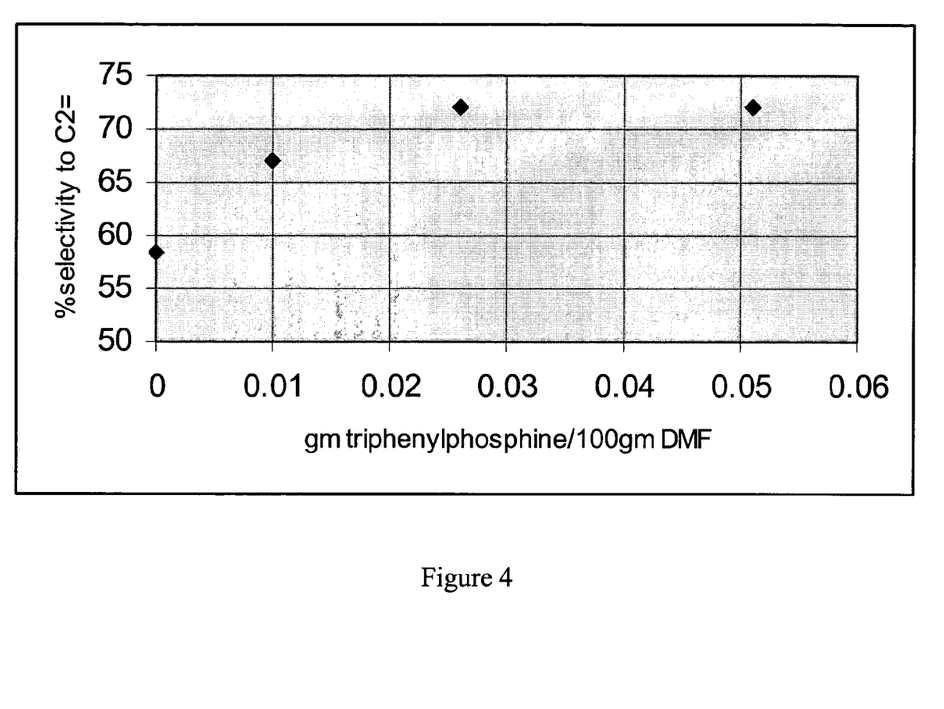
FIG. 4 depicts a plot of the % selectivity to ethylene as a function of the amount of triphenylphosphine in the polar solvent used in an extraction-hydrogenation process.

As illustrated in Table 1, the % acetylene conversion was very high, i.e., greater than 99% in runs 1–10. Further, as demonstrated in FIG. 4, the % selectivity to ethylene increased significantly as the amount of triphenylphosphine in the polar solvent was increased from 0 to about 0.026 gram/100 grams of DMF and increased only slightly as the amount of triphenylphosphine was then increased to about 0.05 gram/100 grams of DMF. As such, the % selectivity to ethylene will mostly likely become constant if the triphenylphosphine concentration is increased even more.

Example 3

This example illustrates performing an extraction-hydrogenation process in which DMF/benzothiophene is used as the polar solvent to remove acetylene from a hydrocarbon stream, and the extracted acetylene is converted to ethylene. The following procedure was followed in runs 1–4. The catalyst used in Example 2 was washed with DMF several times until the DMF appeared colorless, and the DMF was drained from the catalyst. Then 0.0101 gram of benzothiophene additive was dissolved in 1.68 grams of DMF, followed by charging the resulting mixture into the product separator. Next, 100 grams of fresh DMF were added to the product separator. The mixture in the product separator was then circulated through the reactor at a flow rate of 2.0 mL/min. A feed gas containing about 1.8 wt. % acetylene and about 45 wt. % ethylene, all by weight of the total feed, was passed into the reactor at 400 mL/min and 200 psig. Also, a stream of hydrogen was passed into the reactor at a flow rate of 12 cc/min. Additional components contained in the feed gas are shown in Table 2 below. The DMF/benzothiophene solvent extracted acetylene from the feed gas such that the acetylene was dissolved in the liquid phase. As the acetylene in the DMF/benzothiophene solvent contacted the catalyst, it was hydrogenated to ethylene, which desorbed from the liquid phase. The reaction pressure for runs 1–4 was 200 psig. As shown in Table 2 below, the % acetylene conversion and the % selectivity to acetylene were very good in runs 1–4.

Runs 5 and 6 were performed to determine the adsorption capacity of the DMF. The same procedure was followed for runs 5 and 6 except that the reactor was purged with $N_2$ for 4 hours to remove all of the $H_2$ before supplying the feed gas to the reactor. Also, the flow rate of the DMF mixture being circulated through the reactor was 2.7 mL/min. As can be seen in Table 2 below, the effluent streams for runs 5 and 6 contained about 0.6 mol % acetylene and about 0.9 mol % acetylene, respectively, indicating that only a portion of the acetylene was adsorbed by the DMF. The on-stream times of runs 5 and 6 were, respectively, 1 hr 31 min. and 2 hr 28 min. The results of run 5 and 6 show that DMF alone has a diminishing adsorption capacity for acetylene over time as it becomes saturated with acetylene. In order for the solvent to continuously reduce the acetylene in the feed to a very low level, the adsorbed acetylene must be stripped from the rich solvent by some solvent recovery process. The hydrogenation component of the extraction-hydrogenation process serves the function of continuous regeneration of the solvent by converting the acetylene to ethylene.

TABLE 2

|  | Feed Stream | Run #1 Effluent Stream | Run #2 Effluent Stream | Run #3 Effluent Stream | Run #4 Effluent Stream | Run #5 Effluent Stream | Run #6 Effluent Stream |
|---|---|---|---|---|---|---|---|
| Temperature, °F. |  | 251 | 252 | 257 | 262 | 72 | 72 |
| C6+, mole % | 0.000 | 0.003 | 0.004 | 0.005 | 0.006 | 0.003 | 0.004 |
| Methane, mole % | 53.453 | 53.702 | 53.464 | 53.300 | 53.336 | 54.675 | 53.759 |
| Ethane + Ethylene, mole % | 44.735 | 46.247 | 46.454 | 46.631 | 46.588 | 44.718 | 45.331 |
| Acetylene, mole % | 1.812 | 0.006 | 0.006 | 0.006 | 0.004 | 0.604 | 0.906 |

TABLE 2-continued

|  | Feed Stream | Run #1 Effluent Stream | Run #2 Effluent Stream | Run #3 Effluent Stream | Run #4 Effluent Stream | Run #5 Effluent Stream | Run #6 Effluent Stream |
|---|---|---|---|---|---|---|---|
| Butane, mole % | 0.000 | 0.000 | 0.000 | 0.000 | 0.000 | 0.000 | 0.000 |
| 1-butene, mole % | 0.000 | 0.025 | 0.031 | 0.041 | 0.043 | 0.000 | 0.000 |
| Trans-2-butene, mole % | 0.000 | 0.012 | 0.015 | 0.016 | 0.019 | 0.000 | 0.000 |
| Cis-2-butene, mole % | 0.000 | 0.005 | 0.007 | 0.007 | 0.008 | 0.000 | 0.000 |
| Ethylene/Ethane molar ratio | 1376.733 | 111.778 | 116.180 | 123.482 | 128.807 | 1009.512 | 1818.478 |
| DMF recycle rate, cc/min. |  | 2.000 | 2.000 | 2.000 | 1.700 | 2.700 | 2.700 |
| Benzothiophene, (g/100 g DMF) |  | 0.0101 | 0.0101 | 0.0101 | 0.0101 | 0.0101 | 0.0101 |
| % Selectivity to ethylene |  | 74.44 | 73.98 | 73.97 | 74.20 | 99.02 | 100.83 |
| % Acetylene conversion |  | 99.67 | 99.67 | 99.67 | 99.78 | 66.67 | 50.00 |

Example 4

This example illustrates performing an extraction-hydrogenation process in which NMP is used as the polar solvent to extract acetylene from an ethylene stream, and the extracted acetylene is converted to ethylene. Eight runs were performed in accordance with the following procedure. Ten mL of a Pd/Ag catalyst containing 0.3 wt % Pd and 1.6 wt % Ag on an alpha alumina support was placed in a ½ inch ID Stainless Steel reactor, all weight percentages being based on the weight of the total catalyst. The catalyst was washed twice with 300 mL of fresh NMP. Then 200 mL of the NMP was added to the product separator. The catalyst was reduced overnight under a 100 cc/min flow of hydrogen at 100 psig. After allowing the reactor to cool, the NMP was subsequently circulated through the reactor at a flow rate of 2.1 cc/min. A feed gas containing about 1.3 mole % acetylene and 43 mole % ethylene, based on the moles of the total feed, was passed into the reactor at a flow rate of 400 cc/min. Also, a stream of hydrogen was passed into the reactor at a flow rate of 12 cc/min, and the reactor was operated at a pressure of 200 psig. The NMP solvent extracted acetylene from the feed gas such that the acetylene became dissolved in the liquid phase. As the acetylene in the NMP contacted the catalyst, it was hydrogenated to ethylene, which desorbed from the liquid phase into the gas phase. Additional details regarding runs 1–8 are illustrated in Table 3 below.

TABLE 3

|  | Feed Stream | Run #1 Effluent Stream | Run #2 Effluent Stream | Run #3 Effluent Stream | Run #4 Effluent Stream | Run #5 Effluent Stream | Run #6 Effluent Stream | Run #7 Effluent Stream | #8 Effluent Stream |
|---|---|---|---|---|---|---|---|---|---|
| Temperature, ° F. |  | 238 | 237 | 247 | 224 | 223 | 223 | 226 | 224 |
| C6+, mole % | 0 | 0.000 | 0.000 | 0.002 | 0.004 | 0.005 | 0.005 | 0.006 | 0.007 |
| Methane, mole % | 55.269 | 55.838 | 55.308 | 55.129 | 58.952 | 55.086 | 55.100 | 54.960 | 55.010 |
| Ethane + Ethylene, mole % | 43.466 | 44.111 | 44.631 | 44.794 | 41.024 | 44.864 | 44.838 | 44.986 | 44.934 |
| Acetylene, mole % | 1.265 | 0.032 | 0.035 | 0.040 | 0.003 | 0.010 | 0.016 | 0.006 | 0.008 |
| Butane, mole % | 0 | 0.000 | 0.000 | 0.000 | 0.005 | 0.000 | 0.000 | 0.000 | 0.000 |
| 1-butene, mole % | 0 | 0.013 | 0.018 | 0.025 | 0.010 | 0.024 | 0.027 | 0.028 | 0.030 |
| Trans-2-butene, mole % | 0 | 0.006 | 0.008 | 0.010 | 0.005 | 0.011 | 0.013 | 0.015 | 0.014 |
| Cis-2-butene, mole % | 0 | 0.000 | 0.000 | 0.000 | 0.000 | 0.000 | 0.000 | 0.005 | 0.005 |
| Ethylene/Ethane molar ratio | 355.6579 | 100.883 | 108.242 | 103.629 | 68.912 | 98.566 | 103.885 | 43.430 | 52.836 |
| NMP recycle rate, cc/min. |  | 2.100 | 2.100 | 2.100 | 2.100 | 2.100 | 2.100 | 2.100 | 2.100 |
| % Selectivity to C2 |  | 71.69 | 72.46 | 69.29 | 59.99 | 68.23 | 69.12 | 21.63 | 35.50 |
| % Acetylene conversion |  | 97.47 | 97.23 | 96.84 | 99.76 | 99.21 | 98.74 | 99.53 | 99.37 |

As shown in Table 3, the % acetylene conversion was higher in the runs where the reaction temperature ranged from 223° F. to 226° F. (i.e., runs 4–8) than in the runs where the reaction temperature ranged from 237° F. to 247° F. (i.e., runs 1–3). However, the % selectivity to ethylene was better in the first two runs than in the other runs.

What is claimed is:

1. A method of producing monoolefins, comprising:
   (a) contacting an olefin stream with a polar solvent and a high boiling additive such that a highly unsaturated hydrocarbon in the olefin stream becomes dissolved in the polar solvent and the high boiling additive; and
   (b) contacting the polar solvent and the high boiling additive with a hydrogenation catalyst comprising palladium and silver in the presence of hydrogen at conditions effective to hydrogenate the highly unsaturated hydrocarbon to a monoolefin,
   wherein the polar solvent comprises a compound selected from the group consisting of N-methylpyrrolidone, formamide, N-methylformamide, N-ethylformamide, N-phenylformamide, N,N-dimethylformamide, N,N-diethylformamide, N,N-diphenylformamide, sulfolane, n-formyl morpholine, glycerol, triethylene, glycerol, tetraethylene glycerol, and combinations thereof.

2. The method of claim 1, wherein step (b) comprises feeding both the olefin stream and the polar solvent having the highly unsaturated hydrocarbon dissolved therein to a hydrogenation reactor.

3. The method of claim 1, further comprising separating the olefin stream from the polar solvent having the highly unsaturated hydrocarbon dissolved therein before performing step (b).

4. The method of claim 1, wherein a weight ratio of the polar solvent to the highly unsaturated hydrocarbon ranges from about 0.00006 to about 0.15.

5. The method of claim 1, wherein the olefin stream comprises cracked gas recovered from an ethylene cracker.

6. The method of claim 1, wherein the olefin stream primarily comprises ethylene separated from cracked gas.

7. The method of claim 1, wherein the olefin stream primarily comprises propylene separated from cracked gas.

8. The method of claim 1, wherein the highly unsaturated hydrocarbon comprises a compound selected from the group consisting of an acetylene, a diolefin, and combinations thereof.

9. The method of claim 1, wherein the highly unsaturated hydrocarbon comprises a compound selected from the group consisting of acetylene, methylacetylene, vinylacetylene, ethylacetylene, 2-butyne, propadiene, butadiene, isoprene, 1–3 pentadienes, cyclopentadiene, and combinations thereof.

10. The method of claim 1, wherein the hydrogenation catalyst further comprises fluorine.

11. The method of claim 1, wherein the high boiling additive is combined with the polar solvent before said contacting the olefin stream with the polar solvent.

12. The method of claim 11, wherein a mixture of the polar solvent and the high boiling additive comprises from about 0.0001 to about 10 wt. % of the high boiling additive based on the total weight of the mixture.

13. The method of claim 12, wherein a selectivity to the monoolefin during the hydrogenation is greater than about 30%.

14. The method of claim 12, wherein a selectivity to the monoolefin during the hydrogenation is greater than about 80%.

15. The method of claim 11, wherein a mixture of the polar solvent and the high boiling additive comprises from about 0.001 to about 1 wt. % of the high boiling additive based on the total weight of the mixture.

16. The method of claim 11, wherein a mixture of the polar solvent and the high boiling additive comprises from about 0.01 to about 0.1 wt. % of the high boiling additive based on the total weight of the mixture.

17. The method of claim 11, wherein the high boiling additive comprises a compound selected from the group consisting of triphenylphosphine, diphenyiphosphine, benzothiophene, dibenzothiophenc, substituted dibenzothiophenes, pyridine, substituted pyridines, aniline, substituted anilinea, alkali metal fluorides, and combinations thereof.

18. The method of claim 11, wherein the high boiling additive is present in the polar solvent during the hydrogenation.

19. The method of claim 11, wherein the monoolefin desorbs from the polar solvent, and further comprising recycling the polar solvent comprising the high boiling point additive for use in removing the highly unsaturated hydrocarbon from the olefin stream.

20. The method of claim 1, wherein a molar ratio of the hydrogen to the highly unsaturated hydrocarbon is in a range of from about 0.5 to about 20.

21. The method of claim 1, wherein a molar ratio of the hydrogen to the highly unsaturated hydrocarbon is in a range of from about 2 to about 5.

22. The method of claim 1, wherein the highly unsaturated hydrocarbon is acetylene and the monoolefin is ethylene.

23. The method of claim 1, wherein the monoolefin desorbs from the polar solvent.

24. The method of claim 23, further comprising introducing the monoolefin to the olefin stream from which the highly unsaturated hydrocarbon has been removed.

25. The method of claim 23, further comprising recycling the polar solvent for use in removing the highly unsaturated hydrocarbon from the olefin stream.

26. The method of claim 23, wherein the hydrogenation occurs in a liquid phase and the monoolefin desorbs from the liquid phase into a gas phase.

27. The method of claim 1, wherein the monoolefin desorbs from the polar solvent and combines with the olefin stream in situ.

28. The method of claim 1, wherein the polar solvent removes all or a portion of any oligomers formed on the hydrogenation catalyst during hydrogenation.

29. The method of claim 1, wherein the hydrocarbon stream comprises one or more streams from an ethylene cracker.

30. A method of removing a highly unsaturated hydrocarbon from a hydrocarbon stream, comprising:
(a) extracting the highly unsaturated hydrocarbon from the hydrocarbon stream with a polar solvents and a high additive, wherein the polar solvent comprises a compound selected from the group consisting of N-methylpyrrolidone, formamide, N-methylformamide, N-ethylformamide, N-phenylformamide, N,N-dimethylformamide, N,N-diethylformamide, N,N-diphenylformamide, sulfolane, n-formyl morpholine, glycerol, triethylene glycerol, tetracthylene glycerol,and combinations thereof; and
(b) hydrogenating the highly unsaturated hydrocarbon in the polar solvent to a monoolefin via contact wit a hydrogenation catalyst comprising palladium and silver.

31. The method of claim 30, further comprising separating the polar solvent from the hydrocarbon stream prior to hydrogenation.

32. The method of claim 31, further comprising recovering the monoolefin and adding the monoolefin to the hydrocarbon stream.

33. The method of claim 31, further comprising recycling the polar solvent for use in step (a).

34. The method of claim 30, wherein step (b) comprises feeding both the hydrocarbon stream and the polar solvent to a hydrogenation reactor.

35. The method of claim 34, wherein the monoolefin desorbs from the polar solvent and combines with the hydrocarbon stream in situ after step (b), and further comprising separating the polar solvent from the hydrocarbon stream.

36. The method of claim 35, further comprising recycling the polar solvent for use in step (a).

37. A method of producing monoolefins, comprising:
(a) contacting an olefin stream with a polar solvent such that a highly unsalurated hydrocarbon in the olefin stream becomes dissolved in the polar solvent, wherein the polar solvent comprises a compound selected from the group consisting of sulfolane, glycerol, triethylene glycerol, tetraethylene glycerol, and combinations thereof; and (b) contacting the polar solvent with a hydrogenation catalyst comprising palladium and silver in the presence of hydrogen at conditions effective to hydrogenate the highly unsaturated hydrocarbon to a monoolefin.

38. The method of claim 37, wherein step (b) comprises feeding both the olefin stream and the polar solvent having the highly unsaturated hydrocarbon dissolved therein to a hydrogenation reactor.

39. The method of claim 37, further comprising separating the olefin stream from the polar solvent having the highly unsaturated hydrocarbon dissolved therein before performing step (b).

40. The method of claim 37, wherein the hydrogenation catalyst further comprises fluorine.

41. The method of claim 37, wherein the monoolefin desorbs from the polar solvent.

42. The method of claim 41, further comprising introducing the monoolefin to the olefin stream from which the highly unsaturated hydrocarbon has been removed.

43. The method of claim 41, further comprising recycling the polar solvent for use in removing the highly unsaturated hydrocarbon from the olefin stream.

44. The method or claim 37, wherein the monoolefin desorbs from the polar solvent and combines with the olefin stream in situ.

45. The method of claim 37, wherein a weight ratio of the polar solvent to the highly unsaturated hydrocarbon ranges from about 0.00006 to about 0.15.

46. The method of claim 37, wherein the olefin stream comprises cracked gas recovered from an ethylene cracker.

47. The method of claim 37, wherein the olefin stream primarily comprises ethylene separated from cracked gas.

48. The method of claim 37, wherein the olefin stream primarily comprises propylene separated from cracked gas.

49. The method of claim 37, wherein the highly unsaturated hydrocarbon comprises a compound selected from the group consisting of an acetylene, a diolefin, and combinations thereof.

* * * * *